United States Patent
Lehmann et al.

(10) Patent No.: US 7,598,093 B2
(45) Date of Patent: Oct. 6, 2009

(54) NANOPARTICLE AND MICROPARTICLE BASED DETECTION OF CELLULAR PRODUCTS

(75) Inventors: Paul V. Lehmann, Cleveland Heights, OH (US); Alexey Y. Karulin, Mayfield Heights, OH (US); Thomas Oliver Kleen, Shaker Heights, OH (US)

(73) Assignee: CTL Analyzers, LLC, Shaker Heights, OH (US)

( * ) Notice: Subject to any disclaimer, the term of this patent is extended or adjusted under 35 U.S.C. 154(b) by 530 days.

(21) Appl. No.: 10/897,767

(22) Filed: Jul. 22, 2004

(65) Prior Publication Data

US 2005/0277159 A1 Dec. 15, 2005

Related U.S. Application Data

(60) Provisional application No. 60/489,451, filed on Jul. 23, 2003.

(51) Int. Cl.
*G01N 33/543* (2006.01)

(52) U.S. Cl. .............................. 436/523; 435/2; 435/6; 435/7.1; 435/7.5; 435/7.92; 435/7.94; 435/172; 435/287.2; 435/374; 436/506; 436/507; 436/524; 436/528; 436/546; 436/177; 422/82.05; 422/82.08

(58) Field of Classification Search .................. 435/2, 435/6, 7.1, 7.5, 7.23, 7.24, 7.92, 172, 375, 435/287.2, 436, 501, 506, 507, 512, 513, 435/546, 177, 548, 356, 317, 422, 82.08, 435/7.94; 436/501, 506, 507, 512, 513, 523–534, 436/546, 63, 177, 548; 356/317; 422/82.08, 422/82.05
See application file for complete search history.

(56) References Cited

U.S. PATENT DOCUMENTS

| | | | |
|---|---|---|---|
| 5,200,312 A | 4/1993 | Oprandy | 435/5 |
| 5,635,363 A | 6/1997 | Altman et al. | 435/7.24 |
| 5,939,281 A | 8/1999 | Lehmann et al. | 435/7.94 |
| 6,270,772 B1 | 8/2001 | Burrows et al. | 424/193.1 |

(Continued)

FOREIGN PATENT DOCUMENTS

WO  WO 0068692 A  11/2000

OTHER PUBLICATIONS

Martins et al., Determination of Cytokine Responses Using a Multiplexed Fluorescent Microsphere ImmunoAssay, Clinical Chemistry, AM J Pathol (2002) 118: 346-353*

(Continued)

*Primary Examiner*—Gailene R Gabel
(74) *Attorney, Agent, or Firm*—D. Benjamin Borson

(57) ABSTRACT

Embodiments of the present invention relate to devices and methods for detecting cellular products using detection particles having product-specific detection reagents and having a characteristic spectral feature. In particular, devices and methods are provided for measuring secreted cellular products including cytokines. Detection substrates, include microwells having product-specific capture reagents thereon or comprising hydrophobic membranes are described having greater capability to detect products from individual cells in a mixture of heterogeneous cells. With the use of multiple detection particles, multiple cellular products can be detected in a single well. Additionally, using the inherent spectral properties of detection particles, no enzymatic reactions are needed to visualize a secreted product, thereby increasing the sensitivity, reproducibility and ease of use.

53 Claims, 5 Drawing Sheets

U.S. PATENT DOCUMENTS

| | | | |
|---|---|---|---|
| 6,410,252 B1 | 6/2002 | Lehmann et al. | 435/7.94 |
| 6,630,307 B2 * | 10/2003 | Bruchez et al. | 435/6 |
| 6,824,986 B1 * | 11/2004 | Finkelman et al. | 435/7.1 |

OTHER PUBLICATIONS

Martins et al., Determination of Cytokine Responses Using a Multiplexed Fluorescent Microsphere Immunoassay, Clinical Chemistry, Am J Clin Pathol (2002) 118: 346-353).*

Benecky et al., Detection of Hepatitis B surface antigen in whole blood by coupled particle light scattering (Copalis), Clinical Chemistry, 43 (9): 1764-1770 (1997).*

Gebauer et al., Evolution of the Enzyme-Linked Immunosorbent Spot Assay for Post-Transplant Alloreactivity as a Potentially Useful Immune Monitoring Tool (American Journal of Transplantation 2: 857-866 (2002).*

Martins, Thomas B. et al., "Determination of Cytokine Responses Using A Multiplexed Fluorescent Microsphere Immunoassay," *American Journal of Clinical Pathology*, vol. 118, No. 3; Sep. 2002, pp. 346-353; XP009046835.

Goldman, Ellen R. et al., "Avidin: A Natural Bridge For Quantum Dot-Antibody Cojugates," *Journal Of The American Chemical Society, American Chemical Society, Washington, DC US*, vol. 124, No. 22; Jun. 5, 2002, pp. 6378-6382; XP002308426.

Hall, Michael et al., "High Sensitivity Immunoassays Using Particulate Fluorescent Labels," *Analytical Biochemistry*, vol. 272, No. 2; Aug. 1, 1999, pp. 165-170; XP002326859.

Kellar, Kathryn L. et al., "Multiplexed Microsphere-Based Flow Cytometric Assays," *Experimental Hematology* (New York) vol. 30, No. 11, Nov. 2002, pp. 1227-1237; XP002326860.

Watson, Andy et al., "Lighting Up Cells With Quantum Dots," *Biotechniques*, vol. 34 No. 2, Feb. 2003, pp. 296-303; XP009046820.

Hricik, Donald E. et al., "Enzyme Linked Immunosorbent Spot (ELISPOT) Assay For Interferon-Gamma Independently Predicts Renal Function In Kidney Transplant Recipients," *American Journal of Transplantation: Official Journal Of The American Society Of Transplantation And The American Society Of Transplant Surgeons*, Jul. 2003, vol. 3, No. 7, pp. 878-884; XP002326861.

Gebauer, Britta S. et al., "Evolution Of The Enzyme-Linked Immunosorbent Spot Assay For Post-Transplant Alloreactivity As A Potentially Useful Immune Monitoring Tool," *American Journal of Transplantation: Official Journal Of The American Society Of Transplantation And The American Society Of Transplant Surgeons*, vol. 2, No. 9, Oct. 2002, pp. 857-866; XP002326862.

Herr, W. et al., "The Use Of Computer-Assisted Video Image Analysis For The Quantification of CD8<+> T Lymphocytes Producing Tumor Necrosis Factor Alpha Spots In Response To Peptide Antigens," *Journal of Immunological Methods, Elsevier Science Publishers B.V.*, Amsterdam, NL, vol. 203, No. 2, Apr. 25, 1997, pp. 141-152; X[004117425.

Benecky, Michael, J. et al., "Detection Of Hepatitis B Surface Antigen In Whole Blood By Coupled Particle Light Scattering (Copalis)" *Clinical Chemistry*, vol. 43, No. 9, 1997, pp. 1764-1770; XP002326863.

Shams, Homayoun et al., "Contribution of $CD8^+T$ Cells to Gamma Interferon Production in Human Tuberculosis," *Infection and Immunity*, May 2001, vol. 69, No. 5, p. 3497-3501.

Chouaib, Salem et al., "Interleukin 12 Induces The Differentiation of Major Histocompatibility Complex Class I-Primed Cytotoxice T-Lymphocyte Precursors Into Allospecific Cytotoxic Effectors," *Proc. Natl. Acad. Sci. USA*, vol. 91, Dec. 1994, pp. 12659-12663.

Merville, Pierre et al., "Detection of Single Cells Secretign IFN-Gamma, IL-6, and IL-10 in Irreversibly Rejected Human Kidney Allografts, and Theri Modulation by IL-2 and IL-4," *Transplantation*, vol. 55, No. 3, Mar. 1993, pp. 639-646.

Sedgwick, Jonathon D. et al., "Detection of Cell-Surface Molecules, Secreted Products of Single Cells and Cellular Proliferation by Enzyme Immunoassay," *Journal of Immunological Methods*, 150 (1992), pp. 159-175.

Arvilommi, H., "ELISPOT for Detecting Antibody-Secreting Cells in Response to Infections and Vaccination," *APMIS*, 104, 1996, pp. 401-410.

Wu, et al.; "Immunofluorescent labeling of cancer marker Her2 and other cellular targets with semiconductor quantum dots"; Nature Biotechnology, Jan. 2003, vol. 21, pp. 41-46.

* cited by examiner

NANOPARTICLE AND MICROPARTICLE BASED DETECTION OF CELLULAR PRODUCTS

RELATED APPLICATION

This application claims priority under 35 U.S.C. section 119(e) to U.S. Provisional Patent Application Ser. No. 60/489,451, filed Jul. 23, 2003, Paul Lehmann and Alexey Y. Karulin, titled "Microsphere Based Detection of Cellular Products." This application is herein incorporated fully by reference.

FIELD OF THE INVENTION

The present invention relates to devices and methods for detecting secreted cellular products, and in particular for measuring secreted soluble cell products using nanoparticles and/or microparticles with associated capture reagents that recognize the cellular product.

BACKGROUND

Over the last thirty years, the immune system has been studied with better and better laboratory tools. Still, most knowledge of the immune response concerns antibody formation. This is understandable given that antibodies, including specific antibodies, are easily detectable in quantity in the serum of immunized individuals. Antibodies are products of B-lymphocytes ("B cells" or "B-cells"). Antibody production by individual B cells (as well as cells fused with B cells such as hybridomas) is also readily achieved in vitro using a variety of tests, including the ELISA spot assay (also called "ELISPOT" for "enzyme-linked immunospot"). See Segwick, J. D. and Holt, P. G., "A solid-Phase Immunoenzymatic Technique for the Enumeration of Specific Antibody-Secreting Cells," J. Immunol. Methods 57:301-309 (1983). See also Mazer, B. D. et al., "An ELISA Spot Assay for Quantitation of Human Immunoglobulin Secreting Cells," J. Allergy Clin. Immunol. 88:235-243 (1991).

In a conventional B cell ELISA spot assay, standard, commercially-available plates are coated overnight with antigen or animal antibody. In the case where antibody is used, it is typically an "anti-antibody" (e.g., goat antibody reactive with human IgG, IgE, IgM, etc.). After blocking overnight, B cells are introduced in the wells. Following a sufficient culture period, the wells are washed free of the cells and an antibody-enzyme conjugate is added. The plates are then developed using substrate for the enzyme of the conjugate. Spots are counted using a microscope. The lowest amount of detectable antibody is typically in the range of 10 to 50 picograms. See e.g., Renz, H. et al., "Enhancement of IgE Production by Anti-CD40 Antibody in Atopic Dermatitis," J. Allergy Clin. Immunol. 93:658-668 (1994).

In contrast to the antibody response, the response of T-lymphocytes ("T-cells" or T Cells") to antigen (including the antigen of pathogens) can not be easily monitored due to the fact that antigen reactive T cells occur in low frequencies and the fact that their secretory products are not typically stable (i.e. have a short half-life). Indeed, even in hyperimmunized individuals, antigen reactive T cells constitute I in 10,000 cells or less in the peripheral T cell pool, for example, the T cells in circulating blood. Thus, T cells usually act beyond the detection limits of conventional assay systems (such as proliferation assays).

As a consequence of this, there are few sensitive, reliable and rapid techniques at present available that would reliably measure whether a patient has generated a T cell response to a particular pathogen, such as HIV. There is no reliable assay that can detect whether a T cell response to HIV proteins has been generated, what proteins of the virus are primarily targeted, and which determinants within that protein are immunodominant. There is also no reliable method available for testing the magnitude of the anti-viral T cell response (clonal sizes) and its quality (e.g. whether the response is pro- or anti-inflammatory).

Heterogeneity of T cells, their products and the mode of function provide great challenges (particularly as compared to B cells). With respect to mode of function, T cells can act in different subpopulations that utilize strikingly different effector functions. T cell responses can be pro-inflammatory T helper 1 type, Th1, characterized by the secretion of interferon gamma (IFN$\gamma$) and interleukin 2 (IL-2). Th1 cells are critical for the cellular defense and provide little help for antibody secretion. (Strong Th1 responses are usually associated with poor antibody production, which highlights the importance of directly measuring the T cell response instead of relying on antibody measurements.) The other class of T cell responses is antiinflammatory, mediated by Th2 cells that produce IL-4, 5, 10, but no IL-2 or IFN$\gamma$. Th2 cells are the helper cells for antibody production. CD4+ and CD8+ cells both occur in these subpopulations: Th1/Th2:CD4, TC1/TC2:CD8.

Importantly, for each type of infection there is an "appropriate" (and different) type of T cell response (e.g., Th1 vs. Th2, CD4+ vs. CD8+) that clears the infectious agent but does not cause excessive tissue destruction to the host. It is detrimental to the host if an "inappropriate" type of T cell response is engaged (Th1 instead of Th2 or vice versa). Thus, there is a strong need for assessing the host's T cell immunity to the virus to understand the host-virus interplay and to design vaccines. An ideal assay should permit monitoring all of the critical features of the T cell response: first, the existence of a response, i.e., that effector cells have been generated, second the nature of the effector cells as Th1 or Th2 type cells, and finally the magnitude of the response.

Some attempts have been made to apply the B-cell ELISA spot technology to T cells. However, the conventional cytokine ELISA spot assay has not been a more sensitive tool than alternative assays (e.g. proliferation assays), displaying high background and generally a weak signal. The conventional ELISA spot assay for 1 T cells involves plates containing nitrocellulose membranes that are pre-coated with a capture antibody specific for the cytokine to be detected. See e.g., Taguchi, T. et al., "Detection of Individual Mouse Splenic T Cells Producing IFN$\gamma$ and IL-5 Using the Enzyme-Linked Immunospot (ELISPOT) Assay," J. Immunol. Methods 128: 65-73 (1990). See also Fujihashi, F. et al., "Cytokine-Specific ELISPOT Assay," J. Immunol. Methods 160:181-189 (1993). See also Miyahira, Y. et al., "Quantification of Antigen Specific CD8+ T Cells Using an ELISPOT Assay," J. Immunol. Methods 181:45-54 (1995). T cells are plated with the test antigen and start to secrete the type of cytokine they are programmed to produce. As the cytokine is released, it is captured around the secreting cells by the plate bound antibody. After 24 h the cell culture is terminated, cells are removed and the plate-bound cytokine is visualized by a second antibody and an enzymatic color reaction.

Ideally, each product-producing cell will be represented as an ELISA spot. However, with conventional assays, sensitivity does not exceed cytokine measurements in the supernatant by ELISA (cytokine measurements in culture supernatants provide a positive result only if more than 1000 cells are present per well). The quantification of the data is also problematic because of background problems and the subjective, visual evaluation. Moreover, because enzymatic reactions are sensitive to time, reagent quality and reaction conditions, there can be variations in results obtained using conventional ELISA or ELISPOT methods. Moreover, conventional 2 or 3-color systems used with conventional ELISA or ELISPOT methods cannot separately resolve individual spectral features of each colored detection reagent. In conventional multicolor assays, development of colors typically is made sequentially, one after another, each followed by washing steps. This procedure is time consuming and because of its complexity is difficult to carry out. Additionally, substrates are not typically fully transparent, so a second substrate may mask an underlying substrate. Moreover, as more substrates are used, the background becomes darker and less controlled. The above problems with conventional ELISA methods therefore make assays of multiple cellular products difficult or impossible.

There is a great need for better assays to measure secreted soluble cell products. Specifically, there is a need for devices and methods with greater capability to detect cytokines from individual cells in a mixture of heterogeneous cells, and for methods that can detect multiple different secreted cytokine cell products within mixtures of such products, and for methods that have increased reliability and reproducibility.

SUMMARY OF THE INVENTION

The present invention relates to devices and methods for detecting cellular products, and in particular for measuring secreted cell products using nanoparticles, microparticles or combinations of nanoparticles and microparticles (collectively termed herein "detection particles") that are associated with capture reagents raised against the cellular product (also know as an "analyte") of interest.

In general, embodiments of this invention comprise a surface having a capture reagent thereon that is specific or selective for the analyte of interest. When an analyte binds to the capture reagent, a detection reagent is then used to bind to the analyte/capture reagent complex. The detection reagent can bind either to the analyte (on a different portion of the molecule than that which the capture reagent binds) or to the complex itself (e.g., antibodies raised against a capture reagent/analyte pair). Such types of assays are referred to herein as "direct" assays. In some embodiments, the detection reagent includes a nanoparticle or microparticle that has a uniquely defining feature that permits identification and/or quantitation of the amount of the detection reagent present. The identifying feature can be a fluorescent marker, an absorption marker or a phosphorescent marker.

In alternative embodiments, a secondary binding reagent can be used to bind to the capture reagent/analyte pair. In these embodiments, the secondary binding reagent can also have a moiety that is recognized by a detection reagent associated with a nanoparticle or microparticle. Such types of assays are "sandwich" or "indirect" assays.

Regardless of whether the detection is "direct" or "indirect," once a detection reagent is associated (or bound) to the analyte, microscopic or spectroscopic analysis of the detection reagent can be made.

In some embodiments, the surface is a plastic or glass surface of a cell culture dish. In other embodiments, the surface can be a membrane, either a hydrophilic or hydrophobic membrane.

Because the markers used as part of this invention have clearly separate spectral features, one can detect multiple secreted soluble cell products simultaneously, thereby permitting increased speed of analysis and providing ability to compare differences between secreted products from the same cell culture. Further, because no enzyme reaction is needed, the assay devices and methods of this invention have improved reliability and accuracy.

DESCRIPTION OF THE DRAWINGS

FIG. 1 schematically shows one embodiment of the method of the present invention.

DETAILED DESCRIPTION

Figure 1A:
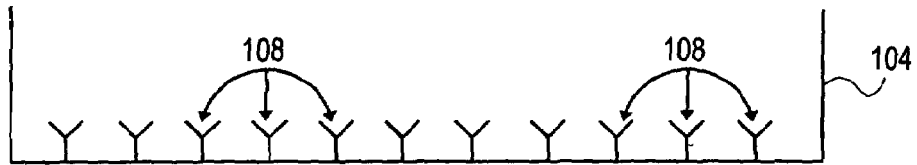
FIG. 1A is a schematic diagram showing a capture reagent ("Y") bound to a surface within a test well.

The present invention relates to devices and methods for detecting cellular products, and in particular for measuring secreted/released cellular products, including cytokines. In general, the devices and methods of this invention can be used to detect any analyte for which there is a capture reagent to associate the cellular product with a detection substrate, a detection reagent that can be attached to a microparticle or nanoparticle (herein termed a "detection particle"). To detect an analyte, the analyte to be detected is associated with a detection substrate, such as a microwell of a plate. In some embodiments, the detection substrate includes a hydrophobic membrane or surface to which a hydrophobic analyte may adhere due to physical interaction with the substrate. In other embodiments, a detection substrate can include one or several analyte-specific ligands, such as antibodies, analyte receptors or combinations of these. Such analyte-specific capture reagent can be associated (e.g., through chemical linking to the surface). Once the analyte is associated with the capture reagent or directly binds to detection surface, a detection particle having a characteristic detection reagent (e.g., antibody analyte specific receptor) is conveniently used. In some embodiments, the detection reagent is an antibody, such as a monoclonal antibody or a polyclonal antiserum. In additional embodiments, a capture reagent is a ligand specific for the analyte of interest. In still other embodiments, a detection particle includes a moiety that can be spectroscopically identified, such as by color, fluorescence, or phosphoresence or other optical feature associated with the detection particle. In some embodiments, the characteristic spectrographic feature is a moiety that is added to the detection particle after its manufacture. In other embodiments, the spectrographic feature is inherently part of the detection particle.

Detection Substrates

The type of detection substrate is not crucial. In some embodiments hydrophilic surfaces can be used. Hydrophilic surfaces can include cell culture dishes of plastic or glass, or hydrophilic membranes (e.g., cellulose). In these embodiments, the analyte specific capture reagent can be attached to the detection surface using chemical means. Means for attaching proteins to a surface are well known in the art (for example using streptavidin/biotin) and need not be described herein further. In some embodiments, regular tissue culture plates can be treated for high protein absorption and/or increased surface area (e.g., corrosion).

The present invention also includes detection substrates that are hydrophobic. In some embodiments a membrane having some hydrophobic characteristics can be used. These embodiments can be especially useful for detection of hydrophobic analytes that need no analyte-specific capture reagent to become adhered to the detection substrate. In one embodiment, membranes are weakly hydrophilic and display advancing contact angles for water between approximately seventy (70) and approximately ninety (90) degrees. In another embodiment, the membranes are hydrophobic and display advancing contact angles for water between approximately ninety (90) and approximately one hundred and thirty (130) degrees. In another embodiment, the membranes are very hydrophobic and display advancing contact angles for water greater than approximately one hundred and thirty (130) degrees.

Capture Reagents

In other embodiments of the invention, a detection substrate can be a microwell pre-coated with a capture reagent selective for a particular cytokine (see FIG. 1A). It is not intended that the present invention be limited by the nature of the capture reagent. In certain embodiments, a capture reagent is a binding ligand such as a capture antibody specific for the materials (analytes) to be detected. In certain embodiments, two or more different analytes can be detected simultaneously (e.g., anti-IFNγ, mAb1 or anti-IL5 mAb or with both simultaneously for a two color assay). In other embodiments, multiple analytes can be detected simultaneously using a single assay substrate. Analyte receptor molecules, such as recombinant receptors, can also be used as capture reagents. Additionally, capture of an analyte can be accomplished using physical association, for example, hydrophobic interaction of non-polar or amphipathic analytes on surfaces that are hydrophobic. Thus, all of the capture mechanisms are herein termed "capture means."

Detection Particles

Once a secreted cellular product is associated with a capture reagent or a membrane, one or more detection particles can be added. As an alternative, molecules released by dying or injured cells, such as LDH, could be measured using similar methods. A detection particle can become associated with the analyte, a capture reagent bound to the analyte, or with an analyte/capture reagent complex. Thus, an assay for the secretion of a cellular product includes detection of a type of detection particle that is associated with that particular secretory product. For example, Quantum Dot Corporation produces particles that can be adapted for use with the devices and methods of this invention. Further description of such particles is provided in Wu et al., Nature Biotechnology 21(4):41-46 (January 2003) and Watson et al., Biotechniques 34:296-303 (February 2003), each reference incorporated herein fully by reference.

The only requirement for a detection particle material is that it be suitable for associating a capture reagent with the detection particle without loss of the capture reagent's ability to bind to an analyte, and that it be compatible with the cells or other components of the test system. Thus, detection particles can comprise organic polymers, inorganic semiconductors or heavy metals. For example, organic polymers include polycarbonates, polyacrylamides, polyacroleins, polystyrenes and the like. Inorganic semiconductors include silicon dioxide-containing materials, cadmium selenide (CdSe) and the like. The only requirement for polymers and semiconductors is that they have a characteristic emission or absorption spectral feature that permits their detection. Thus, colored organic polymers can appear blue, green or red, or in between. In certain embodiments the emission "color" can depend upon the size of the detection particle. Thus, very small particles can fluoresce in the ultraviolet (UV) range, particles of intermediate size can fluoresce in the green portion of the spectrum, and large detection particles can fluoresce in the red or infrared (IR) portions of the spectrum.

The size or shape of a detection particle is not, in general limited. However, it can be convenient to use particles of sufficient size and shape to produce a detectable signal that defines the particle. Thus, nanoparticles, microparticles, nanospheres, microspheres or other shaped particles can be used. As used herein, the term "nanoparticle" generally refers to particles having sizes with a lower limit of about 90 Å and an upper limit of about 500 Å. The term "microparticles" generally refers to particles having sizes in the range of about 0.05μ to about 5μ.

Heavy metals include gold, silver, platinum, palladium, lead and the like. It can be appreciated that any heavy metal that can provide contrast between the unlabeled portion of the detection substrate and the detection particle can be advantageously used.

Thus, to associate metal detection particles, sulfhydryl reagents, such as thiols, and in some embodiments, di-thiols can be used. It is known that certain metals, such as silver, gold and the like, can bind to sulfhydryl (—SH) groups. It is also known that certain proteins (e.g., antibodies and receptor proteins) can bind to —SH groups. Thus, by the use of a di-sulfhydryl reagent such as a di-thiol, detection reagents can be associated with detection particles, thereby forming a detection reagent/capture reagent detection particle. However, it can be appreciated that other types of attachment can be used.

It is also known that certain plastics, such as styrenes, polycarbonates and the like can bind to proteins, such as antibodies and receptors. Regardless of the type of detection particle used or the type of coupling chemistry used to associate the detection particles with the capture antibody, this invention contemplates using all types of materials and coupling chemistries.

Complexes of Detection Reagents and Detection Particles

In certain embodiments, a detection reagent can be coupled conveniently to a detection particle. In some of these embodiments, streptavidin and biotin can be used. In general, a detection particle having straptavidin thereon is reacted with a biotinylated detection reagent (e.g., an antibody) to produce a complex suitable for use in an assay of this invention. One advantage of streptavidin biotin systems is that one can vary the detection particle and the detection reagent as desired with the same coupling chemistry. It is therefore easy to produce a wide variety of detection particle/detection reagent complexes to suit any particular need.

In certain embodiments, such complexes can be made and purified conveniently using a novel purification method. An illustrative example of the method is presented herein as Example 8.

Assays Using Detection Particles

To perform multiple analyses using a single sample, different types of detection particles can be associated with different analytes or capture reagents. Each type of detection particle can be independently detected using a characteristic spectral feature. By detecting the association of a particular type of detection particle with a membrane, multiple cellular products can be simultaneously detected. FIG. 1 depicts an embodiment of the invention.

In some of the descriptions that follow, features of the devices and methods of this invention are described with reference to T-cell cytokines. It is not intended that the scope of this invention be limited to detection of cytokines. Rather, the full scope of the invention includes products secreted by other cell types, for example only, B-cells, epithelial cells, muscle cells, nerve cells, bacterial, fungi, stem cells, endothelial cells, plant cells and the like.

In certain embodiments, freshly isolated, primary cell populations (e.g., lymph node, spleen cells, etc.) are subsequently plated (see FIG. 1B) with the test antigen, (e.g., HIV protein or peptide) and control cultures contain irrelevant antigens or peptides. Since the primary cell suspensions contain abundant antigen-presenting cells (APCs) to process and present the antigen, specific T cells become activated and start to secrete the type of cytokine they are programmed to produce. As the cytokine is released, it is captured around the secreting cells by the plate-bound capture reagent (see FIG. 1B). After a suitable culture period (e.g., between approximately 30 minutes and 48 hours), the cell culture is terminated and the cells are removed (e.g. by washing), leaving the captured, plate-bound secreted product (see FIG. 1C).

It is not intended that the present invention be limited by the nature of the detection reagent. In one embodiment, the detection reagent is a second cytokine-binding ligand (e.g., antibody) free in solution that is conjugated to a detection particle having a secondary detection reagent (e.g., secondary antibody that binds the first detection reagent). In other embodiments, the present invention contemplates the use of directly labeled detection reagents (e.g. antibodies coupled to detection particles). Each cytokine-producing cell will be represented as a spot. In broad aspects of this invention, detection by detection particles may appear similar to an ELISA spot ("ELISPOT"). However, with the use of detection particles, it is not necessary to use an enzyme substrate, as needed for an ELISA assay.

In still other embodiments, the detection particle can be directly labeled with a fluorochrome (e.g., FITC, PE or texas red) or with colored beads (different colors for different secretory products). It can also be labeled with a ligand such as streptavidin-biotin, which can be detected with tertiary reagent that is labeled as above (i.e. with a fluorochrome or bead).

While certain embodiments of the present invention employ, as a first capture reagent, cytokine-binding antibodies bound to a detection surface, the present invention also contemplates the binding of soluble products directly to a membrane without the use of capture reagents. In still other embodiments, the present invention contemplates non-antibody ligands such as cytokine receptors as a capture ligand.

The present invention also contemplates testing devices comprising a plurality of areas on a detection substrate, such as a culture dish including 96-well plates or 360 microwell plates, In a specific embodiment, the present invention contemplates a method of detecting secreted/released T cell cytokines or other products of a cell, comprising: a) providing: i) a detection substrate or detection surface comprising at least one capture reagent; ii) a cell population capable of secreting products or inducing their release, b) adding the cell population to a microwell under conditions such that said cell secretes/releases molecules that bind to the capture reagent; c) adding a detection particle, which binds to the cellular secreted product, and (d) detecting the presence of the detection particle.

The present invention further contemplates embodiments wherein said detection substrate further comprises, prior to said adding of step (b), a test antigen (such as a peptide). Such antigens can be used to test either the specificity of reaction of the analyte to the capture reagent or the specificity of reaction of the detection reagent to the analyte, capture reagent or the analyte/capture reagent complex.

Detection of Cell Products, Including Cytokines

With the present invention one can obtain very clear signals (which are readily suited for image analysis) where previously signals were ambiguous or not detectable at all. One can detect simultaneously several cytokines being produced by T cells. Indeed, the detecting several secretory T cell products at single cell resolution represents a major development in monitoring T cell responses.

While particularly suitable for measuring T cell products such as cytokines, it is also not intended that the invention be limited to the type of sample. The present invention can be employed with success with all types of liquid samples, including various different suspensions of biological material.

Figure 1B:
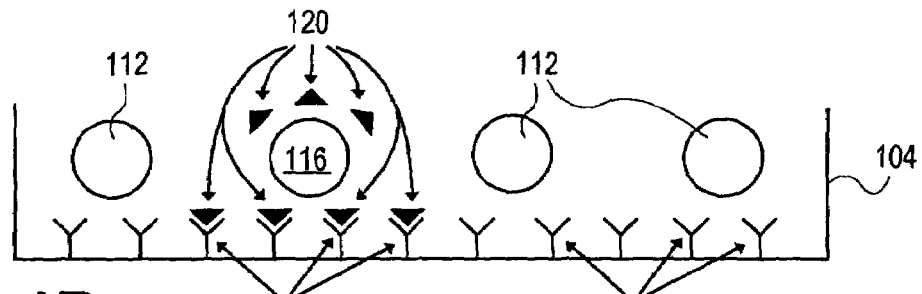
FIG. 1B is a schematic drawing showing cells in solution secreting soluble products (solid black diamonds) binding to the immobilized capture reagent.
Figure 1C:
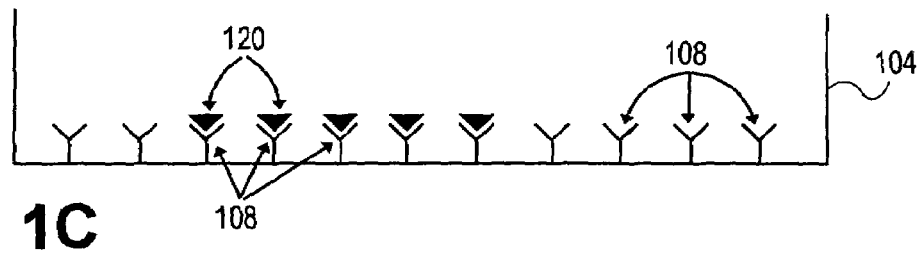
FIG. 1C is a schematic diagram showing surface bound secreted product.
Figure 1D:
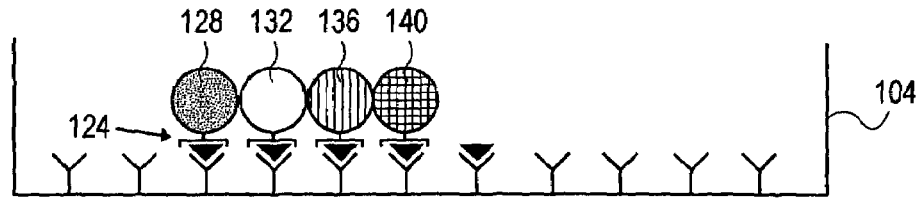
FIG. 1D is a schematic diagram showing binding of four detection reagents coupled directly to 4 different types of detection particles. Each detection particle has a characteristic spectral feature.

In accordance with one embodiment 100 of the invention, as depicted in FIG. 1A a microwell 104 is pre-coated with a first capture reagent 108. In some embodiments, the capture reagent is a cytokine capture antibody specific for the cytokine to be detected (e.g., anti-IFNγ mAb or anti-IL5 mAb or with both simultaneously for the two color assay) or receptors. As depicted in FIG. 1B, certain antigen-exposed cells 112 do not secrete any soluble cell product. However, as shown in FIG. 1C, other, antigen-stimulated cells 120 produce soluble cellular product 124 into the medium. As the product 124 is released, some is captured around the secreting cells by the capture reagent 108. After a suitable culture period (e.g., between approximately 30 minutes and 48 hours), the cells are removed (e.g. by washing), leaving the captured, plate-bound secreted product (see FIG. 1C). FIG. 1D depicts an embodiment of this invention in which four different detection particles are shown (128, 132, 136, and 140) respectively. Each of detection particles 128, 132, 136, and 140 are associated with a detection reagent 124. In this Figure, detection particles 128, 132, 136, and 140 each become associated with the same analyte 120. The differences in the detection particles 128, 132, 136, and 140 reflect differences in characteristic spectrographic features, thereby permitting their differential detection. It can be appreciated that there is no stringent upper limit to the numbers of different cell products (analytes) that can be detected using methods of this invention. In some embodiments, it can be desirable to detect only a single cell product. In other embodiments, it can be desirable to detect 2, 3, 4, 5, 6, 7, 8, 9, 10, or more, such as 15, 20, 30, 50 or even 100 different products in a single assay. The only requirement is that sufficient cell product be present in the sample to permit sufficiently intense spectrographic signals to be produced by each of the multiplicity of detection particles.

Figure 1E:
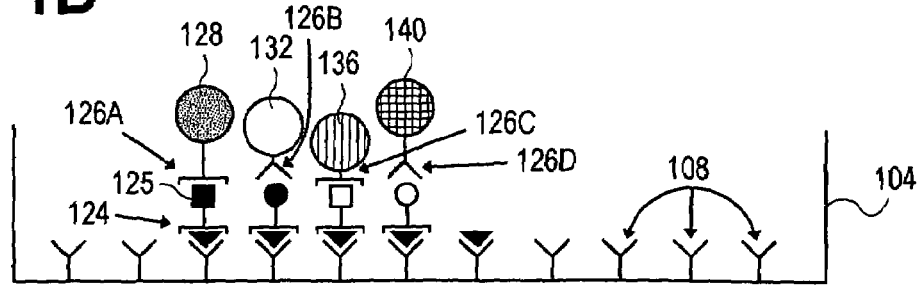
FIG. 1E is a schematic drawing showing binding of four detection reagents coupled indirectly to each of the 4 detection particles via a secondary detection reagent.

FIG. 1E depicts an alternative embodiment of this invention in which 4 detection particles are shown associated with the analyte via a secondary detection reagent 125 (e.g., a secondary antibody).

Figure 1F:
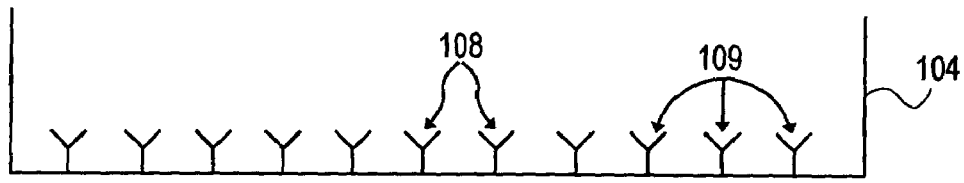
FIG. 1F depicts an alternative embodiment 101 having two types of capture reagents 108 and 109 that are specific for different secreted cellular products.

FIG. 1F depicts an alternative embodiment 101 having two types of capture reagents 108 and 109 that are specific for different secreted cellular products.

Figure 1G:
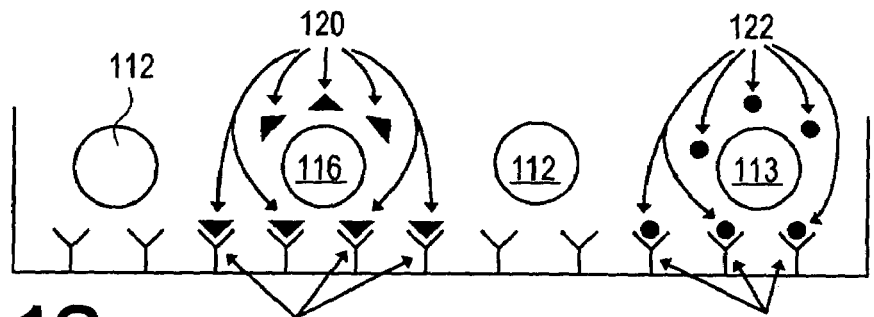
FIG. 1G depicts an embodiment wherein two cells 116 and 113 are stimulated to produce products 120 and 122, respectively.

FIG. 1G depicts an embodiment wherein two cells 116 and 113 are stimulated to produce products 120 and 122, respectively.

Figure 1H:
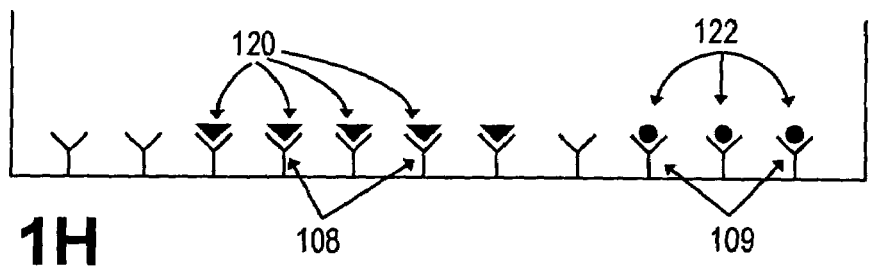
FIG. 1H depicts an embodiment of the invention in which cells 116 and 113 have been removed, leaving their secreted products 120 and 122 bound to capture reagents 108 and 109, respectively.

FIG. 1H depicts an embodiment of the invention in which cells 116 and 113 have been removed, leaving secreted products 120 and 122 bound to capture reagents 108 and 109, respectively.

Figure 1I:
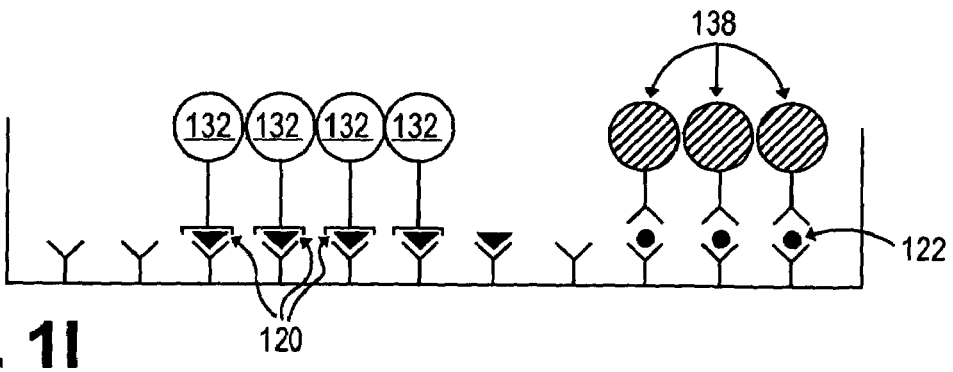
FIG. 1I depicts multiple product assay embodiment in which detection particles 132 and 138 are shown bound to products 120 and 122, respectively.

FIG. 1I depicts a multiple product assay embodiment in which detection particles 132 and 138 are shown bound to products 120 and 122, respectively.

Figure 2:
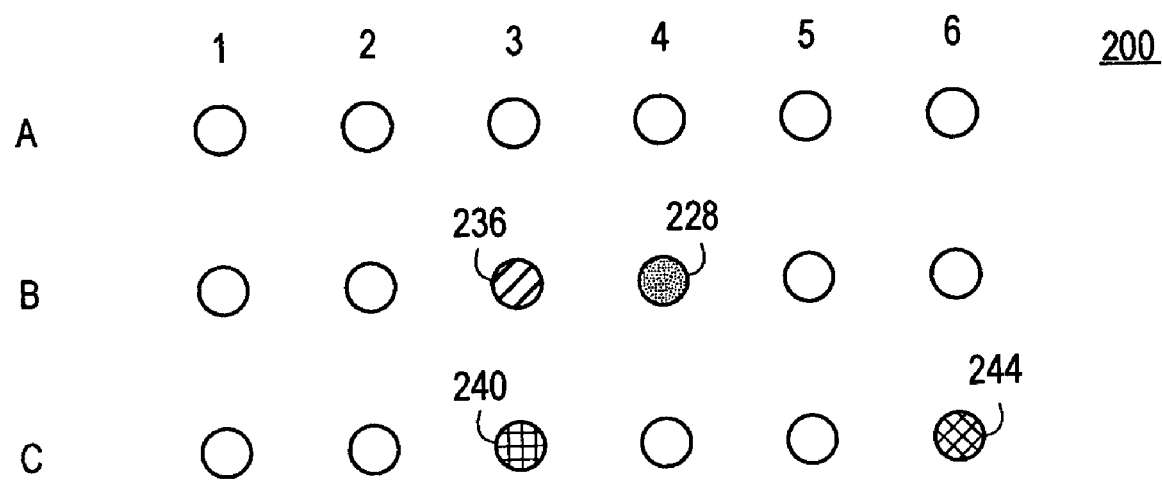
FIG. 2 depicts a schematic drawing of an embodiment of this invention in which a number of different wells are decorated with detection reagent-bound particles of this invention.

FIG. 2 depicts an embodiment 200, which represents a portion of a multiwell plate having 6 columns (1 to 6) of wells in 3 rows (A to C). Wells A1-A6 have no labeled materials therein. Well B3 is depicted as having detection particle 236 therein, and well B4 is depicted as having detection particle 228 therein. Well C3 is depicted as having detection particle 240 therein, and well C6 is shown as a positive control.

TABLE 1

| Name | Abbr. | Type | Specific Types |
|---|---|---|---|
| Interferons | IFN | alpha | Leukocyte Interferon |
| | | beta | Fibroblast Interferon |
| | | gamma | Macrophage Activation Factor |
| Interleukins | IL-1 | 1 alpha | Endogenous Pyrogen |
| | | 1 beta | Lymphocyte-Activating Factor |
| | | 1 ra | IL-1 Receptor Antagonist |
| | IL-2 | | T-cell Growth Factor |
| | IL-3 | | Mast Cell Growth Factor |
| | IL-4 | | B-cell Growth Factor |
| | IL-5 | | Eosinophil Differentiation Factor |
| | IL-6 | | Hybridoma Growth Factor |
| | IL-7 | | Lymphopoietin |
| | IL-8 | | Granulocyte Chemotactic Protein |
| | IL-9 | | Megakaryoblast Growth Factor |
| | IL-10 | | Cytokine Synthesis Inhibitor Factor |
| | IL-11 | | Stromal Cell-Derived Cytokine |
| | IL-12 | | Natural Killer Cell Stimulatory Factor |
| Tumor Necrosis Factors | TNF | alpha | Cachectin |
| | | beta | Lymphotoxin |
| Colony Stimulating Factors | CSF | GM-CSF | Granulocyte-macrophage Colony-Stimulating Factor |
| | | Mp-CSF | Macrophage Growth Factor |
| | | G-CSF | Granulocyte Colony-stimulating Factor |
| | | EPO | Erythropoietin |
| Transforming Growth Factor | TGF | beta 1 | Cartilage-inducing Factor |
| | | beta 2 | Epstein-Barr Virus-inducing Factor |
| | | beta 3 | Tissue-derived Growth Factor |
| Other Growth Factors | LIF | | Leukemia Inhibitory Factor |
| | MIF | | Macrophage Migration-inhibiting Factor |

TABLE 1-continued

| Name | Abbr. | Type | Specific Types |
|---|---|---|---|
| | MCP | | Monocyte Chemoattractant Protein |
| | EGF | | Epidermal Growth Factor |
| | PDGF | | Platelet-derived Growth Factor |
| | FGF | alpha | Acidic Fibroblast Growth Factor |
| | | beta | Basic Fibroblast Growth Factor |
| | ILGF | | Insulin-like Growth Factor |
| | NGF | | Nerve Growth Factor |
| | BCGF | | B-cell Growth Factor |

In addition to those products listed above in Table 1, other products include IL-13, IL-15, IL-16, IL-17, IL-18, IL-23, GranzymeB, Perforin and RANTES.

A captured molecule can be visualized by a detection reagent associated with a detection particle. It is not intended that the present invention be limited by the nature of the detection reagent or the detection particle. In one series of embodiments, the detection reagent is a second cytokine binding ligand (e.g., antibody or receptor) free in solution that is conjugated to a detection particle. Regardless of the type of detection reagent used, once the cell product is associated with a specific type of detection reagent and detection particle, detection of the detection particle reveals the presence of the analyte.

It is not intended that the present invention be limited by the nature of the product to be detected. Cytokines are hormone-like substances secreted by a wide variety of cells, including (but not limited to) lymphocytes (e.g., T cells), macrophages, fibroblasts, and endothelial cells. It is now known that cytokines consist of a broad class of glycoproteins that have the ability to regulate intercellular communication (e.g., cell-cell interaction) in both normal and pathologic situations. Cytokines generally contain from approximately 60 to 200 amino acid residues, with a relative molecular weight of between 15 and 25 kd. At least 35 distinct cytokines have been elucidated (see Table 1 above).

There is also a family of chemo-attractant cytokines known as "chemokines." See e.g. T. J. Schall and K. B. Bacon, "Chemokines, leukocyte trafficking, and inflammation" *Curr. Op. Immun.* 6:865-873 (1994). These molecules share structural similarities, including four conserved cysteine residues which form disulfide bonds in the tertiary structures of the proteins. The present invention contemplates employing the devices and methods of the present invention for detecting secreted chemokines.

Role of many cytokines are now known. For example, interleukin-1α and interleukin-1β (IL-1α and IL-1β) are distantly related polypeptide hormones that play a central role in the regulation of immune and inflammatory responses. See D. P. Cerretti et al., U.S. Pat. Nos. 4,894,333 and 4,879,374, each hereby incorporated by reference. These two proteins were originally both classified as IL-1, based on a shared lymphocyte activation factor (LAF) activity, and a common major cellular source, activated macrophages. As information has accumulated from studies using purified natural and recombinant IL-1 molecules, it has become clear that IL-1α and IL-1β each mediate most, if not all, of the wide range of activities previously ascribed to IL-1.

TNF-α plays a critical role in the development of acute pulmonary failure and injury. When released into the lung, TNF-α has devastating effects, causing rapid and diffuse tissue injury. This is presumably a direct result of its known effects on endothelial cells and granulocytes, as well as its induction of other mediators such as 1 IL-1, prostaglandins, and platelet-activating factor.

While one series of embodiments of the present invention employ, as a first capture reagent, cytokine binding antibodies bound to detection surface, the present invention also contemplates the binding of soluble products directly to the surface without the use of capture reagents. In still another series of embodiments, the present invention contemplates non-antibody ligands, such as cytokine receptors and lectins (e.g. concanavalin A or lectins), as the capture ligand. With respect to cytokine receptors, the existence of IL-1 plasma membrane receptors which bind both IL-1α and IL-1B is now well-established. IL-1 receptors have now been cloned and expressed in high yield. See S. K. Dower, U.S. Pat. No. 4,968,607, hereby incorporated by reference. Similarly, tumor necrosis factor-α (TNF-α) and TNF-β and their receptors have been isolated, and DNA sequences encoding these secretory proteins are described. See C. A. Smith et al., European Patent Application No. 90309875.4 (Publication No. 0418014A1), hereby incorporated by reference. See also U.S. patent application Ser. Nos. 405,370, 421,417 and 523,635, hereby incorporated by reference.

The present invention also contemplates the use of detection substrates to detect and/or screen synthetic cytokine analogues and inhibitors. Cytokine analogues are those compounds that act in an analogous manner as the known cytokine. An example of such an analogue is described in European Patent Application No. 343684, hereby incorporated by reference. See also U.S. patent application Ser. Nos. 266,531, 199,915, 238,713, 248,521, and 238,171, hereby incorporated by reference. In that case, the analogue is a polypeptide inhibitor of interleukin-1.

Finally, the present invention can be used with success to measure a variety of cellular products other than cytokines. In one embodiment, the present invention contemplates detecting other products of T cells such as perforins and granzymes. Perforin is a lytic protein and granzymes are a family of natural serine proteases; these products are stored in secretory granules until released from the cell. See e.g. G. Berke, "The CTL's Kiss of Death" Cell 81:9-12 (1995).

The present invention also contemplates measuring products from cells other than T cells. For example, the device and method of the present invention can be employed to detect the expression and secretion of recombinant products from host cells. Further, the devices and methods of this invention can be used to detect non-secreted materials associated with cell membranes. As described above, cells can be grown in conditions favoring their adherence to a membrane having a capture reagent specific for the analyte to be detected. An analyte can be bound to a cell membrane, such as an integral membrane protein, and after a suitable time in culture, the cell can be removed from the membrane using lytic methods. Lytic methods include use of detergents, such as TWEEN 80 TM, lipid solvents such as acetone or an alcohol, or alternatively, the cells can be ruptured by hypoosmotic shock, for example using distilled water. Once the cell contents are washed away, residual, undesired membrane components can be removed with the use of solvents or detergents followed by washing. Thus, the dominant materials left adhered to the membrane are those bound to a specific capture reagent. Analysis of those materials can be accomplished using methods described herein.

The methods described herein are also suitable for measuring molecules released by dying cells. When T cells kill a target cell, the contents of the killed cell spill and can be captured around the dieing cell. In this way, the number of cells killed can be exactly enumerated.

The present invention also includes devices and methods for detecting alloimmune responses, and in particular, as a measurement of potential allograft rejection in the field of human organ transplantation.

In this regard, it should be stressed that up to 30-40% of transplanted organs are lost over 5 years, mostly due to chronic rejection. Importantly, present HLA matching procedures are based on defining serological or structural differences between HLA alleles, but do not reveal any functional information regarding potential alloreactivity. Detectable single amino acid differences between HLA alleles may, or may not, be clinically important. There is thus a clear need for improved techniques that can provide predictive functional information above and beyond the present typing 1 technologies.

The present state of clinical organ transplantation requires the use of immunosuppressive agents to prevent acute transplant rejection. The exact pharmacological regimen used for immunosuppression varies significantly from one transplant center to the next, but generally includes cyclosporine A, corticosteroids and azathioprine, in some combination. Serum or whole blood cyclosporine levels are used primarily to prevent toxicity and not to evaluate the level of immunosuppression; it is well established that patients with therapeutic cyclosporine levels can develop acute rejection episodes. Additionally, cyclosporine levels do not provide any information about the relative immunosuppressive effects of the other agents used in conjunction with the cyclosporine A. There is presently no method for assessing the immunosuppressive effects of corticosteroids or azathioprine (except to evaluate for signs of clinical toxicity), and medication doses are often adjusted empirically. Thus, as is the case with structural-based assays for tissue typing, there are presently no methods available to functionally assess the quality or quantity of the alloimmune response in transplant recipients.

Embodiments of the present invention can fill this need. It is contemplated that detection particle based assays of the present invention will measure existing and potential human alloimmune responses by accurately detecting and quantifying allospecific cytokine profiles. The assay of the present invention has a number of advantages that make it ideal for the monitoring of T cell activity in vivo. Detection of the cytokine occurs directly at its source, i.e. the secreting cell, before it is diluted, degraded, or absorbed to receptors on a bystander cell, thus making it extremely sensitive. Indeed, the assay can detect single antigen-reactive cells. Secondly, the detection particle based assay measures clonal sizes, defining the frequencies of antigen-reactive, or alloreactive T cells in the bulk population. Since the 24 hour duration of the assay is too short for T cell proliferation to occur in vitro, the frequency of detected T cells is reflective of the in vivo 1 frequency. Thirdly, the assay identifies the cytokine profile of each responding cell. This approach is additionally superior to previously published, time consuming, isolation and characterization of in vitro cultured T cell clones, in that the short incubation time of the microsphere based assay circumvents in vitro artifacts.

The assay of the present invention is very sensitive. This improved sensitivity is central to monitoring alloreactivity in a potentially infrequent responding population: immuno-suppressed transplant recipients. The sensitivity is also central to detecting responses between related and unrelated individuals. By "related" individuals (such as humans) it is meant that such individuals have a common ancestry (e.g. children of the same parents, cousins, etc.). By "unrelated" individuals it is meant that such individuals have no known ancestral relationship.

Embodiments of this invention can also be used in analyses of infections, vaccinations for infections, cancer, and autoimmune disease.

In still further embodiments, kits embodying detection reagents, detection particles and other materials needed to carry out assays of this invention are provided. In general, a kit comprises: (1) one or more detection particles, (2) one or more detection reagents, (3) a solution for preparing a mixture of detection particles and detection reagents, and (4) instructions for use. In other embodiments, a detection substrate can also be supplied.

In particular embodiments, a kit may contain (1) one or more detection particles with streptavidin bound thereto, (2) one or more detection reagents with biotin bound thereto, (3) a reaction vial, (4) a solution for reacting the detection particles with the detection reagents, and (4) instructions for use. In alternative embodiments, a kit may additionally contain one or more agarose particles with straptavidin attached thereto, wherein the agarose particle has sufficiently greater mass to as to be capable of being sedimented under conditions such as centrifugation. Such kits may be prepared with all of the necessary instructions for preparing the materials to be used in an assay and instructions for carrying out the assay procedure.

EXAMPLES

The following examples serve to illustrate certain preferred embodiments and aspects of the present invention and are not to be construed as limiting the scope thereof.

In the experimental disclosure which follows, the following abbreviations apply: eq (equivalents); M (Molar); M (micromolar); N (Normal); mol (moles); mmol (millimoles); μmol (micromoles); nmol (nanomoles); gm (grams); mg (milligrams); μg (micrograms); L (liters); ml (milliliters); μl (microliters); cm (centimeters); mm (millimeters); μm (micrometers); nm (nanometers); ° C. (degrees Centigrade); BD (Becton Dickenson, Bedford, Mass.); ENDO (Endogen, Cambridge, Mass.); PHRM (Pharmingen, San Diego Calif.).

Example 1

Use of Detection Surfaces in Detection Particle Based Assay

In this example, a detection surface is in a microtiter plate to detect cellular products. First, the detection surface is coated with anti-interferon gamma (IFN gamma antibody 1) as the capture reagent. After several hours of incubation (2 hrs to overnight), during which the capture reagent(s) bind(s) to the membrane, excess reagent is washed away. The unsaturated surfaces of the membrane are then blocked with irrelevant protein (bovine serum albumin or gelatin) to prevent subsequent nonspecific binding of proteins. Following the blocking step, the plates are washed to remove non-plate bound, excess blocking reagent.

At this point the detection substrate is properly prepared to test cells. In this case, human peripheral blood mononuclear lymphocytes (PBL) are added at a concentration of about $5 \times 10^5$ per well. Specific antigen (e.g. HIV antigen) is added to the experimental wells, control wells will contain no antigen or irrelevant antigen (e.g. myohemerythrin, a protein that humans have not encountered). Among all cells plated (about $5 \times 10^5$ cells) only the antigen specific T cells will be stimulated by the antigen to release secretory products (e.g. IFN-gamma). In the control wells, in the absence of the antigen, antigen specific cells are not stimulated and do not release secretory products. During a 4-48 hr cell culture period (dependent on the product to be detected) the antigen specific cells secrete their products(s) being captured by the capture reagents around the secreting cell.

Following the culture period, the cells are washed away, leaving their secretory product retained on the membrane. A detection reagent bound to a detection particle is added to bind to the plate-bound secretory product (the detection and capture antibodies specific for secretory products, e.g., IFNγ have to recognize different parts of the molecule such as not to interfere with each other's binding). The detection particle is either directly labeled with a fluorochrome (e.g., FITC, PE or texas red) or has a characteristic spectral feature. (e.g., different spectral features for different cellular products). Directly labeled detection antibodies associated with detection particles are particularly useful. Alternatively, an antibody is added that is specific for the analyte and a secondary antibody is attached to the detection particle. Coupling of detection antibody to the detection particle by biotin-streptavidin can also be used.

The present invention contemplates a variety of means for visualizing the detection particles using a detection reagent such as: a) immune fluorescence if the secondary (or tertiary) reagent was a fluorochrome or b) a characteristic spectral feature (e.g., different "colors" for different analytes) visualized by light microscopy. Each "spot" of colored substrate corresponds to one cell producing or secreting the product. The difference in number of spots between antigen stimulated wells and the number of spots in the negative control wells (with medium alone or irrelevant antigen) establishes the "signal" to be analyzed (usually there is no spot formation in the negative control). Sizes of the spots correspond to the quantity of product secreted, the number of spots establishes the frequency of antigen specific cells in the cell population tested (i.e. cells that were induced by the antigen to secrete the product among all cells plated, e.g., 20 IFN-gamma spots in HIV antigen challenged PBL represent a frequency of 40/million, if $5 \times 10^5$ cells were plated).

Example 2

Peptide Screening

In this example, microwells are employed to screen and identify the antigenic determinants (i.e. MHC-bound peptides of the antigen generated by intracellular processing) that T cells recognize, using peptides. Usually, in studies that involved peptides, a few randomly chosen sequences of the antigen are tested as peptides. However, even overlapping sequences that walk down the molecule in steps of 5 to 10 amino acids do not necessarily detect all determinants. By contrast, in this example overlapping sets of peptides are employed that walk the molecule amino acid by amino acid. This peptide scan includes every possible determinant on an antigen and provides an exact mapping of the T cell repertoire.

While an assay system has been employed to test for antigen specific CD4 cells [G. Gammon et al., "T Cell Determinant Structure: Cores and Determinant Envelopes in Three Mouse Major Histocompatibility Complex Haplotypes" J. Exp. Med. 173: 609-617 (1991)], the present invention allows for testing of CD8 cells. CD8 determinant mapping for HIV identifies possible peptides for vaccines. Determinant mapping for autoantigens in autoimmune disease has prognostic and possible therapeutic consequences.

For determinant mapping, Myelin Basic Protein ("MBP") peptides that walk the MBP molecule amino acids by amino acid are used. These peptides produce clear data in SHIV-ERER mice. The peptides can be frozen without losing bioactivity at 14 µM concentration in HL-1 medium, which is 2× the optimal concentration for the bioassay. Thus, the large number of peptides involved do not have to be diluted and plated for each experiment, but can be freshly thawed from storage. The entire peptide series is diluted, pipetted and frozen series in advance and, on the day of experiment, the required number of plates are prepared.

The number of cells available from patients can be limiting; one million cells can be obtained from one milliliter of blood and usually fifty milliliters of blood is available per patient (i.e., fifty million cells may be the total cells available for the assay). Because $2\times10^5$ cells per well provides clear results with the plate of the present invention, this is sufficient for testing 250 peptides, which constitutes an average size protein. However, by miniaturizing the plates (e.g. to 50 microliter wells), one can test for 1000 peptides, which can cover even the larger proteins. The entire peptide series can be tested on an individual. The plating of the cells can be performed with 12 channel pipettors into the freshly prepared plates, reducing the time involvement on the first day of the assay to a couple of hours.

In this example, PBL cells were plated at $2\times10^5$ cells per well into 96 well microtiter plates containing the hydrophobic membrane pre-coated with an antibody as capture reagent. The cells are incubated in the wells with antigen for 24 h at 37° C., 8% $CO_2$. During this culture period, T cells with specificity for a given peptide are activated and start secreting cytokines and other cellular products, which are captured by the appropriate antibody on the plate around producing cells. Thus, secreting cells (antigen specific memory cells) are surrounded by a "spot" of the cytokine.

After an additional culture (24 hours), the cells are then washed away and the bound cytokine is detected by a biotinylated second antibody that is specific for the same cytokine but recognizes a different determinant on it. The plate bound second antibody is attached to a microsphere with a characteristic marker thereon.

The numbers of spots in antigen containing wells vs. wells containing medium alone or irrelevant antigens establish the number of antigen specific cells in the culture. Since $2\times10^5$ cells are plated to each well, the absolute frequency represents the frequency of antigen reactive T cells in $2\times10^5$ T cells of the given specificity within the cell pool tested.

Example 3

Two Color Detection Particle Based Assay

In this example, a capture surface is prepared as in Example 1, except that a second capture reagent and a second detection reagent/microsphere is used as well. To prepare the surface for a two-color assay, two (2) capture reagents (anti-IFNγ and anti-IL-5 antibody) are used simultaneously (for additional capabilities, still additional capture reagents can be employed for a "multicolor" assay).

Cells are again plated (about $5\times10^5$ cells) and only the antigen specific T cells are stimulated by the antigen to release secretory products. However, in this case, the surface is capable of detecting both IFNγ and IL-5. After the culture period and washing described in Example 1, a second detection reagent attached to a second detection particle is employed together with the first detection reagent attached to a first detection particle. In this case, detection particles labeled with anti-IL-5 are added (alternatively, fluorochromes emitting different colors when excited by UV light permit two or multicolor assays e.g., FITC:green, PE:red). Spots originating from cells that secreted one of the products only, will appear as a single color (e.g., red or blue), while cells secreting both will have the both colors represented by different detection particles.

Example 4

Mixed Lymphocyte Culture

In this example, the detection particle based assay of the present invention is used as a functional measurement of alloimmune responses. Alloresponses are measured in naive responder mouse splenocytes upon stimulation with irradiated allogeneic stimulator splenocytes. A Balb/c ($H-2^d$) anti-SJL ($H-2^s$) mixed lymphocyte response (MLR) is set up by mixing $8\times10^5$ responder splenocytes ($H-2^d$) with $4\times10^5$ irradiated stimulator splenocytes ($H-2^s$) in 200 micro Liter of HL-1 media (serum free), in 96 well plates that were pre-coated with antibodies to IL-2, IL-5 or IFNγ as capture reagents.

A strong proliferative response is detected and the secretion of Th1 (IFN-gamma), but not Th2 (IL-5) cytokines, is measured in culture supernatants. In addition, there is CTL killing of SJL target cells.

The detection particle based assay can be evaluated visually using a microscope or other optical device. The Balb/c ($H-2^d$) anti-SJL ($H-2^s$) response is primarily of a Th1 phenotype, with strong IL-2 and IFN-gamma 10 but essentially no IL-5 production. Control wells with stimulators alone, responders alone, and $H-2^d$ stimulators mixed with syngeneic, irradiated $H-2^d$ responders all reveal no spots for any cytokine. Similar assays are performed in multiple strain combinations with equivalent results, showing that the quality of the response is not strain specific. Quantitative analysis (spots per $10^6$ splenocytes) for each cytokine reveals 180-250 spots per million responder splenocytes plated for both IFNγ and IL-2, while <5 per million IL-5 spots are detected. Notably, these responses are 5-10-fold greater than the antigen-specific responses (which are typically 15-30 spots per million cells) from the same mouse strain.

In order to verify that the assay is quantitatively reliable, a similar detection particle based analysis is performed on serially diluted samples, and we find that the number of responding cells falls linearly in relation to the serial dilution. Thus, the detection particle based assay yields reproducible quantitative and qualitative information regarding the alloimmune response.

Example 5

Human Transplant Recipients

Given the ability of embodiments of the present invention to detect antigen-specific responses, the methods are also suitable for the study of human alloresponses in the transplant setting, including but not limited to the testing of immunosuppressed transplant recipients. The present invention contemplates the use of the microsphere based assay as a) a functional predictor of allograft survival in cadaver and living related renal transplant recipients, and b) a tool for monitoring the level of immunosuppression in renal allograft recipients.

96 well plates are coated with capture reagent for either IL-2, IL-4, IL-5, IL-10, or IFN in PBS. Peripheral blood lymphocytes (PBLs) are prepared from normal human volunteers, mixed in various stimulator/responder ratios in 2 mls of complete RPMI in a 24 well plate. After a 12-72 hour activation (IL-2 and IFN can best be detected at 12-24 hours, while IL-4, IL-5, and IL-10 require 36-72 hours, and more in other embodiments, 48 hours), the cultures are harvested, washed, and added to the precoated plates. After another 24 hours the cells are washed from the plates and second detection antibodies attached to microspheres are added to the wells. The plates are washed after an overnight incubation, and after a final wash, cytokine-specific spots are analyzed by the image analysis computer program as described above.

While it is not intended that the assays of the present invention be limited by the use of particular antibodies, work with human PBLs has resulted in the determination that the antibody combinations set forth in Table 2 can effectively detect human cytokines in recall responses to common antigens.

TABLE 2

| Cytokine | Coating antibody (Capture Reagent) | Detection antibody (Detection Reagent) |
| --- | --- | --- |
| IL-2 | BG-5 (Serotec) | Rabbit polyclonal (BD) |
| IL-4 | 8D4-8 (PHRM) | MP4-25D2 (PHRM) |
| IL-5 | JES1-39D10 (PHRM) | JES1-5A10 (PHRM) |
| IL-10 | JES3-9D7 (PHRM) | JES3-12G8 (PHRM) |
| IFN | MA700 (ENDO) | MA701 (ENDO) |

Blood samples are obtained from normal human volunteers in heparinized green top tubes, and rocked gently at room temperature until ready for use. PBLs are prepared by standard Ficoll Hypaque centrifugation and counted. By these methods, one can obtain between $1 \times 10^6$ and $3 \times 10^6$ PBLs from each milliliter of blood. All experiments are performed using complete RPMI media.

In some instances, T cell enrichment is desirable. T cells can be enriched from PBLs using human T cell isolation columns (R and D Systems), as per manufacturer's recommendations. In other instances, depletion of T cell subtypes is desired. Depletion of T cell subtypes can be performed by standard methods, using OKT3 (anti-CD3), OKT4 (anti-CD4), or OKT8 (anti-CD8), and rabbit complement (Cedarlane, Hornsby Ont). Aliquots of the resultant cells can be washed and stained with FITC conjugated antibodies for phenotyping by FACS. The antibodies are isolated from hydriboma supernatants grown in our laboratory by standard methods.

The alloimmune responses in normal individuals can produce primarily Th1 type cytokines, i.e., IL-2 and IFN, with little IL-4, IL-5 or IL-10. It is expected that detected alloreactive responder frequencies in normal individuals will fall in the range of 0.1-10% of the responding T cells. The results for immunosuppressed individuals may vary, but it is expected that the cytokine production will decrease in strength and the clonal size of the response will also be relatively decreased. With sufficient numbers of normal individuals for comparison, an immunosuppressed individual who shows very little relative decrease in response may show signs of allograft rejection.

Example 6

Two Color Assay for Human IL2 and Human Interferon γ

On day 1 plates (MIP45, Millipore) were coated simultaneously with two primary capture monoclonal antibodies (mAbs), one raised against (1) h-IFN-γ. Endogen MA700A) at a concentration of 4 μg/ml and another raised against h-IL-2 (R&D Systems 5334.21) at a concentration of 3 μg/ml. 200 μl of coating mAbs mixture was added per well. Plates were coated overnight at 4° C.

On day 2 the plates were washed 3 times with PBS (200 μl/well), and blocked with 1% BSA in PBS for 2 h at RT (200 μl/well). PPD antigen was added to the well at concentration 100 μg/ml (100 μl/well). 300.000 human unseparated PBMCs were added to the same wells (100 μl/well). Plates were incubated for 24 h at 37° C., humidified, in the presence of 7% $CO_2$.

On day 3 cells and unbound materials were removed from the wells by washing 3 times with PBS and 3 times with PBS-Tween (0.05%). Then plate was incubated overnight at 4° C. with 100 μl per well of detection particles directly labeled with secondary detection reagents being antibodies. Red dots (655 nm) were labeled with anti h-IFN-γEndogen M701) and used at a concentration $5.0 \times 10^{-9}$ M. Green dots (525 nm) were labeled with h-IL-2 mAbs (Endogen BG5) and used at a concentration of $1.0 \times 10^{-8}$ M.

On day 4 unbound detection particles were washed out 4 times with PBS-Tween (0.05%) and 3 times with PBS. Digital images were taken using a Fluorescent microscope (Optem) with a long-path emission filter (Chroma 32013).

Figure 3:
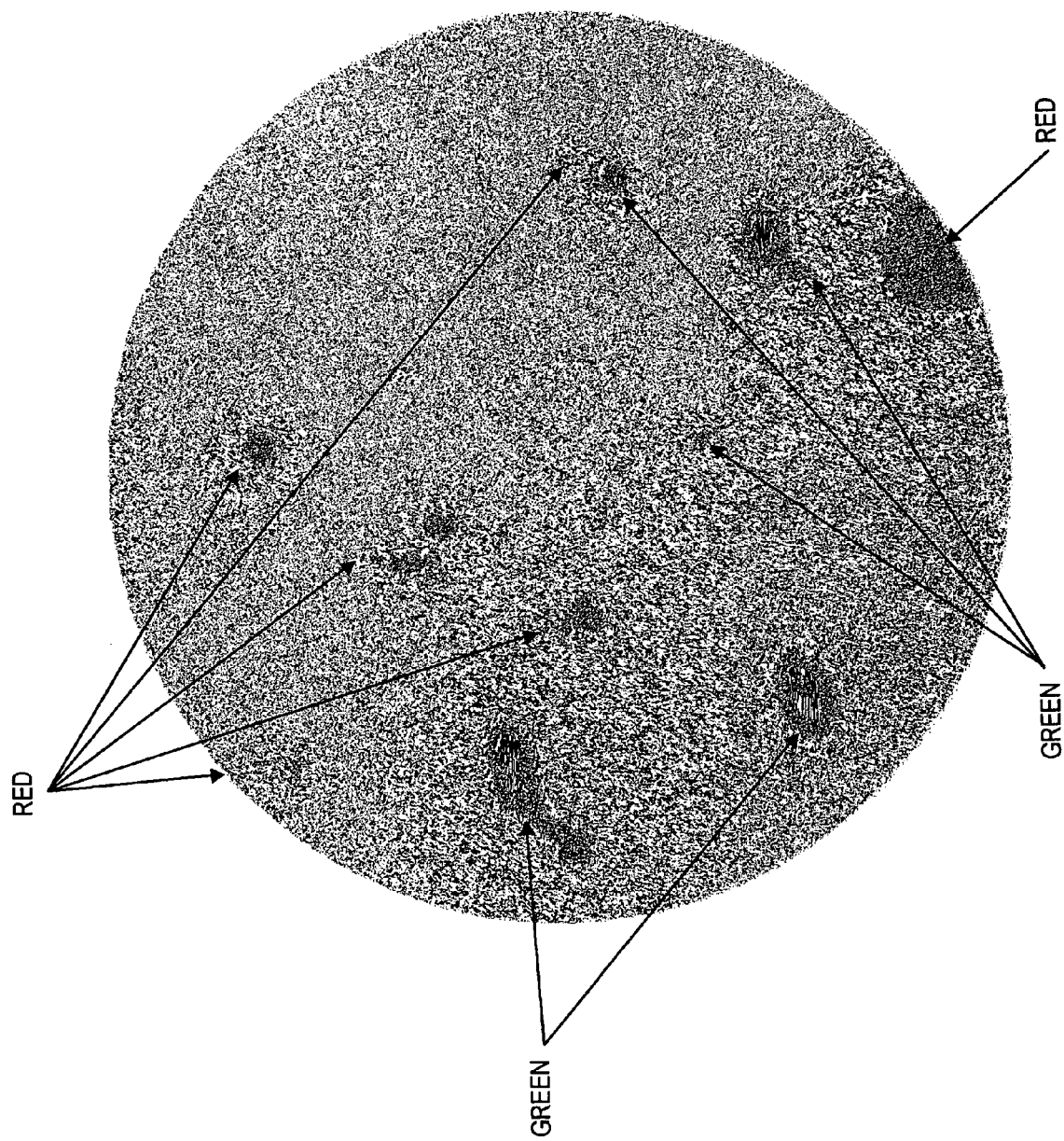
FIG. 3 depicts an assay according to an embodiment of this invention in which two types of detection particles are used.

FIG. 3 depicts results of such a study. A photomicrograph of a well treated as above shows red dots (R) that indicate the presence of secreted h-IFN-γ. Green dots (G) indicate the presence of secreted h-IL-2.

Example 7

Use of Nano-Particles Labeled with Streptavidin for Multicolor Assay of Cell-Secreted Products In other embodiments, methods can be used to substitute particles directly labeled with detection secondary antibodies. It is analogous to the indirect method described here, with the difference that interaction of the streptavidin-labeled particles with biotinylated secondary antibodies takes place prior to their interaction with the cytokine-primary coating antibody complex on the surface.

The method is based on the fact that interaction of streptavidin with its natural ligand, biotin, is practically irreversible; the equilibrium binding constant for this interaction exceeds the magnitude of $10^{11}$ $M^{-1}$.

Particles of each individual type (color) covalently conjugated with streptavidin or its analog, avidin, are premixed with the biotin-labeled secondary detection antibody (reagent) specific to each secreted product. After the reaction is completed, the excess of unbound biotinylated antibodies is removed by the addition of agarose beads coated with streptavidin. Agarose beads with the bound excessive biotinylated antibodies are then removed by centrifugation. Particles of different color, each labeled with single type of the secondary detection antibody (reagent) through streptavidin-biotin interaction, are incubated with the surface-bound secreted product similar to the way directly conjugated particles are used. Several particle types can be used either simultaneously or in a number of consecutive steps.

Example 8

Figure 4:
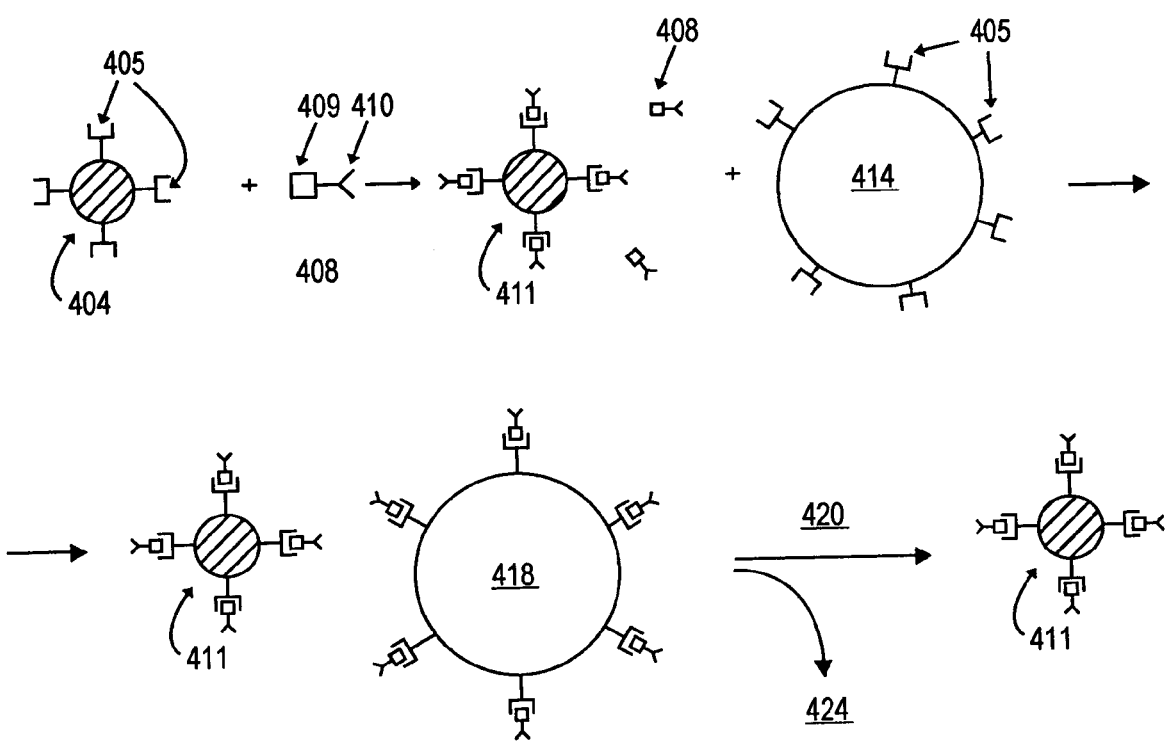
FIG. 4 depicts a diagram for producing purified streptavidin/biotinylated detection particles according to an embodiment of this invention.

Preparation of Purified Detection Particles Labeled with Streptavidin and Biotinylated Detection Antibodies In other embodiments, this invention includes new methods for producing detection particles having detection reagents thereon. An embodiment of this method is illustrated in FIG. 4. A nanoparticle 404 labeled with streptavidin 405 is mixed with biotinylated detection reagent 408 comprising biotin 409 coupled to a detection reagent 410. These are incubated together for sufficient time to permit biotin 409 of biotinylated detection reagent 408 to bind streptavidin 405 on the nanoparticle 404 thereby forming biotinylated streptavidin detection particle complex 411. Some free biotinylated detection reagent 408 is depicted free in solution. Then, an agarose particle 414 having streptavidin 405 thereon is added to the mixture and incubated for a further period of time. The resulting solution contains complexes 411 and agaroselbiotinylated detection reagent complexes 418. Little or no free biotinylated detection reagent 408 is present in the solution. Next, centrifugation step 420 results in sedimentation of agarose/biotinylated detection reagent complexes at 424, leaving biotinylated streptavidin detection particle complexes 411 free in solution. Subsequently, complexes 411 can be used in detection particle based assays.

From the above, it should be clear that the present invention provides improved devices and methods to measure secreted cell products, and in particular, secreted T cell cytokines. The devices and methods of the present invention provide a greater capability to detect cytokines from individual cells in a mixture of heterogeneous cells. The methods also permit more accurate, rapid, reproducible assays that can be used to detect multiple secreted cellular products in the same assay by using multiple detection particles each having a characteristic spectral feature. It can be appreciated that the above descriptions are provided by way of example only, and are not intended to limit the scope of the invention. Persons of ordinary skill can take the teachings of this application and produce modifications and variations that are within the scope of this invention. All of those modifications and variations are considered to be part of this invention.

We claim:
1. A method of detecting a secreted cell product, comprising:
   a) providing a reaction chamber comprising:
      cell culture and detection substrate upon which a cell that produces and secretes the cell product can adhere and a complex formed by the cell product with a detection particle is visualized as a spot on said substrate;
      said detection substrate having capture reagent thereon that binds to said cell product to form a product-capture reagent complex;
   b) adding a sample of cells to said reaction chamber and permitting at least one of said cells to adhere to said substrate;
   c) stimulating said cells to produce said product, wherein said product binds to said capture reagent to form a product-capture reagent complex at a location near said cell on said substrate and then washing away said cells to expose said location;
   d) adding a detection reagent to said reaction chamber, wherein said detection reagent binds to said product producing a detection reagent-cell product-capture reagent complex (DRC);
   e) adding a detection particle to said chamber, wherein said detection particle binds to said detection reagent via streptavidin/biotin binding producing a detection particle-detection reagent-cell product-capture reagent complex (DRCC); and
   f) visualizing said detection particle on said DRCC as a spot on said substrate.

2. The method of claim 1, wherein said capture reagent is a product-specific ligand covalently attached to said substrate.

3. The method of claim 2, wherein said product-specific ligand is an antibody or a product-specific receptor.

4. The method of claim 2, wherein said detection substrate comprises a microwell.

5. The method of claim 1, wherein said capture reagent is a surface, and said product becomes associated with said surface by way of physical interaction.

6. The method of claim 5, wherein said physical interaction is hydrophobic interaction.

7. The method of claim 1, wherein said product is an interferon.

8. The method of claim 7, wherein said interferon is interferon gamma.

9. The method of claim 1, wherein said product is an interleukin.

10. The method of claim 9, wherein said interleukin is IL-5.

11. The method of claim 1, wherein said cell is a human cell.

12. The method of claim 1, wherein said detection particle is a nanoparticle having a lower limit of size of about 90 Å and an upper limit of about 500 Å.

13. The method of claim 1, wherein said detection particle is a microparticle having a lower limit of size of about 0.05 μm; and an upper limit of size of about 5 μm.

14. The method of claim 1, wherein said particle is made of a material selected from the group consisting of organic polymers, inorganic semiconductors and heavy metals.

15. The method of claim 14, wherein said organic polymer is selected from the group consisting of polystyrene, polyacrylamide, polyacrolein and polycarbonate.

16. The method of claim 14 wherein said inorganic semiconductor is selected from the group consisting of silicon dioxide-containing semiconductors and cadmium selenide (CdSe).

17. The method of claim 14, wherein said heavy metal is selected from the group consisting of gold, silver, platinum, palladium, and lead.

18. The method of claim 1, wherein said detection particle exhibits a spectral property selected from the group consisting of absorption, fluorescence and phosphoresence.

19. The method of claim 18, wherein said detection particle exhibits a spectral feature having a lower limit of wavelength in the ultraviolet portion of the spectrum and an upper limit in the infrared portion of the spectrum.

20. A method for determining alloreactivity, comprising
   a) providing a reaction chamber comprising:
      cell culture and detection substrate upon which a cell that produces and secretes the cell product can adhere and a complex formed by the cell product with a detection particle is visualized as a spot on said substrate;

said detection substrate having a capture reagent thereon that binds to said cell product to form a product-capture reagent complex;

b) adding a first cell to said reaction chamber;

c) adding a second cell to said reaction chamber, where at least one of said first cell and said second cell adheres to said substrate, wherein one of said cells stimulates said other of said cells to produce a cellular product, wherein said cellular product binds to said capture reagent to form a product-capture reagent complex at a location near at least one of said cells;

d) washing away said cells to expose said location;

e) adding a detection reagent to said reaction chamber, wherein said detection reagent binds to said product producing a detection reagent cell product-capture reagent complex (DRC);

f) adding said detection particle to said chamber, wherein said detection particle binds to said detection reagent via streptavidin/biotin binding producing a detection particle-detection reagent-cell product-capture reagent complex (DRCC); and g) visualizing said detection particle on said DRCC as a spot on said substrate, wherein presence of a cellular product which results from the one cell stimulating another cell provides indication of alloreactivity.

21. The method of claim 20, wherein said first cell and said second cell are derived from related human beings.

22. The method of claim 20, wherein said first cell and said second cell are derived from unrelated human beings.

23. A method of detecting a plurality of secreted cell products, comprising:

a) providing a reaction chamber comprising:

cell culture and detection substrate upon which cells that produce and secrete the cell products can adhere and complexes formed by the cell products with distinct detection particles are visualized as spots on said substrate;

said detection substrate having a plurality of capture reagents thereon, each of said reagents binds to at least one of said plurality of secreted cell products;

b) adding a sample of cells to said reaction chamber, where at least one of said cells adheres to said substrate;

c) stimulating said cells to produce said plurality of cell products, wherein said products bind to at least two of said capture reagents to form product-capture reagent complexes at a location near at least one of said cells and then washing away said cells to expose said location;

d) adding a plurality of distinct detection reagents to said reaction chamber, wherein each of said detection reagents binds to one type of said cell products forming at least a first complex and a second complex of said cell products and said detection reagents, producing a plurality of detection reagent-cell product-capture reagent complexes (DRC);

e) adding a plurality of types of detection particle to said chamber, wherein each of said types of detection particle binds via streptavidin/biotin binding to only one of said detection reagents producing a plurality of detection particle-detection reagent-cell product-capture reagent complexes (DRCC), and wherein each distinct type of detection particle has a different spectrographic feature associated therewith sufficient to permit differential detection of each of said plurality of complexes; and f) visualizing said plurality of detection particles on said complexes as one or more spots on said substrate.

24. The method of claim 23, wherein each of said plurality of capture reagents comprise antibodies specific for one of said plurality of cell products.

25. The method of claim 23, wherein said capture reagent comprises a surface to which said cell products become associated through physical interaction.

26. The method of claim 25, wherein said physical interaction is hydrophobic interaction.

27. A kit for detecting the presence of a cell product comprising:

a cell culture reaction chamber comprising:

a detection substrate upon which a cell that produces and secretes the cell product can adhere and a complex formed by the cell product with a detection particle is visualized as a spot on said substrate;

said detection substrate having a capture reagent thereon that binds to said cell product forming a product-capture reagent complex;

a detection reagent that binds to said cell product or said product-capture complex;

a detection particle having a characteristic spectrographic feature adapted to bind to said detection reagent via streptavidin/biotin binding to thereby form a detection particle-detection reagent complex;

a solution for mixing said detection particle and a solution for mixing said detection reagent; and instructions for use, said instructions including the following steps:

a) adding a sample of first cells to said reaction chamber, where at least one cell adheres to said substrate;

b) stimulating said cell to produce said product, wherein said product binds to said capture reagent to form a product-capture reagent complex at a location near said cell on said substrate;

c) washing away said cell to expose said location;

d) adding said detection reagent to said reaction chamber, wherein said detection reagent binds to said product, producing a detection reagent-cell product-capture reagent complex (DRC);

e) adding said detection particle to said chamber, wherein said detection particle binds to said DRC, producing a detection particle-detection reagent-cell product-capture reagent complex (DRCC); and f) visualizing said detection particle on said DRCC as a spot on said substrate.

28. The kit of claim 27, further comprising at least one solution suitable for growing cells.

29. The kit of claim 27, wherein said capture reagent is a product-specific ligand covalently attached to said substrate.

30. The kit of claim 29, wherein said product-specific ligand is an antibody or a product-specific receptor.

31. The kit of claim 29, wherein said detection substrate comprises a microwell.

32. The kit of claim 27, wherein said capture reagent is a surface, and said product is adsorbed said surface by way of physical interaction.

33. The kit of claim 32, wherein said physical interaction is hydrophobic interaction.

34. The kit of claim 27, wherein said product is an interferon.

35. The kit of claim 34, wherein said interferon is interferon gamma.

36. The kit of claim 27, wherein said product is an interleukin.

37. The kit of claim 36, wherein said interleukin is IL-5.

38. The kit of claim 27, wherein said cell is a human cell.

39. The kit of claim 27, said instructions further comprising, after step a): adding a second cell to said reaction chamber, wherein one of said first or second_cells stimulates another of said cells to produce a cellular product indicative of alloreactivity, wherein said cellular product binds to said capture reagent.

40. The kit of claim 39 having instructions for use, wherein said first cell and said second cell are derived from related human beings.

41. The kit of claim 39 having instructions for use, wherein said first cell and said second cell are derived from unrelated human beings.

42. The kit of claim 27, wherein said detection particle is a nanoparticle having:
a lower limit of size of about 90 Å; and
an upper limit of about 500 Å.

43. The kit of claim 27, wherein said detection particle is a microparticle having:
a lower limit of size of about 0.05 μm; and
an upper limit of size of about 5 μm.

44. The kit of claim 27, wherein said particle is made of a material selected from the group consisting of organic polymers, inorganic semiconductors and heavy metals.

45. The kit of claim 44, wherein said organic polymer is selected from the group consisting of polystyrene, polyacrylamide, polyacrolein and polycarbonate.

46. The kit of claim 44, wherein said inorganic semiconductor is selected from the group consisting of silicon dioxide-containing semiconductors and cadmium selenide (CdSe).

47. The kit of claim 44, wherein said heavy metal is selected from the group consisting of gold, silver, platinum, palladium, and lead.

48. The kit of claim 27, wherein said detection particle exhibits a spectral property selected from the group consisting of absorption, fluorescence and phosphorescence.

49. The kit of claim 48, wherein said detection particle exhibits a spectral feature having a lower limit of wavelength in the ultraviolet portion of the spectrum and an upper limit in the infrared portion of the spectrum.

50. A kit for detecting the presence of a plurality of secreted cell products, comprising:
a reaction chamber comprising:
a cell culture substrate upon which cells that produce and secrete the cell products can adhere and complexes formed by the cell products with distinct detection particles ate visualized as spots on said substrate;
said substrate having a plurality of capture reagents thereon, that each bind to at least one of said plurality of secreted cell products to form a product-capture reagent complex;
a plurality of detection reagents, that are each adapted to bind to one type of said cell products to thereby from a plurality of detection particle-detection reagent complexes;
a plurality of types of distinct detection particles, wherein each of said types of detection particles binds via streptavidin/biotin binding to only one of said detection reagents to thereby form a plurality of detection particle-detection reagent complexes, and wherein each type of distinct type of detection particles has a spectrographic feature associated therewith sufficient to permit differential detection of each of said plurality of said complexes;
a solution for mixing said plurality of detection reagents and a solution for mixing said plurality of detection particles; and
instructions for use, said instructions including the following steps:
a) adding a sample of cells to said reaction chamber, at least one of said cells adhering to a location on said substrate;
b) stimulating at least one of said cells to produce said plurality of cell products, wherein each of said products binds to at least one of said capture reagents to form product-capture reagent complexes near the location of said cell;
c) washing away said cell to expose said location;
d) adding said plurality of detection reagents to said reaction chamber, wherein each of said detection reagents binds to one type of said cell products, forming a at least a first complex and a second complex of said products and said detection reagents, producing a plurality of detection reagent-cell product-capture reagent complexes (DRC);
e) adding said plurality of types of detection particles to said chamber, wherein each of said types of detection particles binds to only one of said DRC complexes producing a plurality of detection particle-detection reagent-cell product-capture reagent complexes (DRCC); and
f) visualizing said distinct detection particles on said complexes as one or more spots on said substrate.

51. The kit of claim 50, wherein each of said plurality of capture reagents comprise antibodies specific for one of said plurality of cell products.

52. The kit of claim 50, wherein said capture reagents comprise a surface onto which said cell products become adsorbed through physical interaction.

53. The kit of claim 52, wherein said physical interaction is hydrophobic interaction.

* * * * *

UNITED STATES PATENT AND TRADEMARK OFFICE
CERTIFICATE OF CORRECTION

PATENT NO. : 7,598,093 B2  Page 1 of 1
APPLICATION NO. : 10/897767
DATED : October 6, 2009
INVENTOR(S) : Paul V. Lehmann et al.

It is certified that error appears in the above-identified patent and that said Letters Patent is hereby corrected as shown below:

In the claims:

Col. 20, line 61, after "comprising" add -- : --

Col. 20, line 63, before "cell culture" add -- a --

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,598,093 B2
APPLICATION NO. : 10/897767
DATED : October 6, 2009
INVENTOR(S) : Paul V. Lehmann et al.

It is certified that error appears in the above-identified patent and that said Letters Patent is hereby corrected as shown below:

Col. 23, line 3, after "second" remove "_"

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,598,093 B2
APPLICATION NO. : 10/897767
DATED : October 6, 2009
INVENTOR(S) : Lehmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1013 days.

Signed and Sealed this

Fourteenth Day of December, 2010

David J. Kappos
*Director of the United States Patent and Trademark Office*